United States Patent [19]
Holland et al.

[11] Patent Number: 5,277,067
[45] Date of Patent: Jan. 11, 1994

[54] MINIATURE PRESSURE SENSOR AND PRESSURE SENSOR ARRAYS

[75] Inventors: Christopher E. Holland, Redwood City, Calif.; Peter J. Hesketh, Chicago, Ill.

[73] Assignee: Colin Electronics Co., Ltd., Aichi, Japan

[21] Appl. No.: 940,346

[22] Filed: Sep. 3, 1992

Related U.S. Application Data

[62] Division of Ser. No. 563,199, Aug. 6, 1990, Pat. No. 5,163,328.

[51] Int. Cl.$^5$ ............................ G10L 7/08; G10L 9/00
[52] U.S. Cl. .......................................... 73/723; 73/717; 73/753; 73/862.625; 313/310
[58] Field of Search ........... 73/717, 723, 753, 862.625, 73/862.68; 29/25.17, 25.18; 128/672; 313/309, 310

[56] References Cited

U.S. PATENT DOCUMENTS 4,638,669 1/1987 Chou .................................. 73/517 R

OTHER PUBLICATIONS

Spindt et al., "Physical Properties of Thin-Film Field Emission Cathodes with Molybdenum Cones", *Journal of Applied Physics*, vol. 47, No. 12, Dec. 1976, pp. 5248–5263.
Hansma, "Scanning Tunneling Microscopy", *J. Appl. Phys.* 61 (2), Jan. 15, 1987, pp. R1–R23.
Kenny et al, "Micromachined Silicon Tunnel Sensor for Motion Detection", Appl. Phys. Lett. vol. 58, No. 1, pp. 100–102, Jan. 7, 1991.
Green et al, "Vacuum Integrated Circuits", *IEDM Tech. Dig.*, p. 172, 1985.
Dayton et al, "Ultra Small Electron Beam Amplifiers", *IEDM Tech. Dig.*, p. 780, 1986.
Busta et al, "Field Emission from Tungsten-Clad Silicon Pyramids", *IEEE Trans. Electron Devices*, vol. 36, p. 2679, 1989.
Brodie, "Physical Considerations in Vacuum Microelectronics Devices", *IEEE Trans. Electron Devices*, vol. 36, p. 2641, 1989.
Spindt et al, "Field-emitter Arrays Applied to Vacuum Flourescent Display", *IEEE Trans. Electron Devices*, vol. 36, p. 225, 1989.
Hsien-Chung Lee et al, "Simulation and Design of Field Emitter Array", *IEEE Trans. Electron Devices Lett.*, vol. 11, p. 579, 1990.

(List continued on next page.)

*Primary Examiner*—Donald O. Woodiel
*Attorney, Agent, or Firm*—Oliff & Berridge

[57] ABSTRACT

An improved pressure sensor element and pressure sensor array is formed by a cathode layer, a cathode tip attached to the cathode layer, and an anode layer opposing the cathode layer. The magnitude of the electron current flowing between the cathode tip and the anode layer is dependant on the field strength at the cathode tip, which is dependant on the separation between the cathode tip and the anode layer. As a deflectable anode layer is deflected towards the cathode tip, the field strength increases, causing a corresponding change in the magnitude of the flow of electrons. The cathode tip is separated from the anode layer such that electron current is produced at relatively low voltages by tunneling or field emission. The exact method of current production is selected by controlling the initial separation between the anode layer and the cathode tip. Pressure sensor elements are produced using a series of fabrication processes including forming a hole in an insulating layer deposited on the cathode layer, depositing a cathode having a cathode tip into the hole thus formed, and bonding the anode layer onto the insulating layer, thereby forming a pressure sensor element. A plurality of pressure sensor elements are fabricated into pressure sensor arrays by this method. Pressure sensor elements or pressure sensor arrays are thus produced at low cost.

22 Claims, 10 Drawing Sheets

OTHER PUBLICATIONS

Thomas et al, "Fabrication and Some Applications of Large-area Silicon Field Emission Arrays", *Solid State Electronics*, vol. 17, p. 155, 1974.

Allen, "Silicon Field Emitter Arrays: Fabrication and Operation", *Proceeding of the Second International Conference on Vacuum Microelectronics*, p. 17, Jul. 1989.

Bin et al, "CAPPSS: A Thin Diaphragm Capacitive Pressure Sensor Simulator, ", *Sensors and Actuators*, vol. 11, p. 1, 1987.

Baski et al, "Tunnelling Accelerometer", *Journal of Microscopy*, vol. 152, P 1, Oct. 1988, pp. 73-76.

Waltman et al, "An Electron Tunneling Sensor", *Sensors and Actuators*, pp. 201-210, 1989.

Wandass et al, "Magnetic Field Sensing With Magnetostrictive Materials Using A Tunneling Tip Detector", *Sensors and Actuators*, pp. 211-225, 1989.

MINIATURE PRESSURE SENSOR AND PRESSURE SENSOR ARRAYS

This is a division of application Ser. No. 07/563,199 filed Aug. 6, 1990, now U.S. Pat. No. 5,163,338.

FIELD OF THE INVENTION

The present invention relates generally to pressure sensors and more specifically to arrays of, and methods for manufacturing, pressure sensors for measuring pressure profiles and determining spatial pressure distributions for medical applications.

BACKGROUND OF THE INVENTION

There are many applications where accurate measurement of pressure requires the use of miniaturized pressure sensors, including monitoring of physiological parameters, process monitoring of industrial facilities and automobile performance monitoring. In medical applications, miniaturized sensors are used for both invasive and non-invasive measurement of blood pressure as well as measurement of other body pressures for diagnostic purposes. In many instances, improved monitoring of the parameters of interest requires the use of closely spaced sensing devices. Blood pressure measurement by tonometry, for example, requires pressure sensors narrower than the underlying artery and is facilitated by sensor element spacing smaller than the artery width.

Many of the pressure sensors employed for medical monitoring are based on strain gage or capacitance measurement techniques. U.S. Pat. No. 4,881,410, for example, discloses a silicon pressure sensor based on capacitance measurement which requires fabricating a sophisticated structure of metal and silicon on the surface of a chip. The pressure sensitivity of the device is controlled by scaling the dimensions of the sensor. U.S. Pat. No. 4,771,638 discloses a pressure sensor operating on the strain gage principle. Sensors such as those described above are generally built in layers parallel to the underlying substrate of the micro chip. The large surface areas needed by these conventional sensors to produce signals large enough for accurate measurement limits the density of pressure sensing devices on the chip surface.

Although field emitter arrays have been used in semiconductor devices, e.g., U.S. Pat. Nos. 4,721,885 and 4,835,438, and have also been used as electron sources in semiconductor and cathode ray tube (CRT) displays, e.g., U.S. Pat. No. 4,766,340, heretofore pressure sensors have not been produced using such a technique or incorporating such a device.

SUMMARY OF THE INVENTION

Accordingly, one object of the present invention is to provide an improved pressure sensor.

Another object of the present invention is to provide an improved pressure sensor array wherein the density of pressure sensors per unit area can be increased.

A further object of the present invention is to provide an improved pressure sensor particularly suited for medical diagnostic applications.

A still further object of the present invention is to provide a sensor device or sensor array easily adapted to be responsive to a variety of external stimuli.

Another object of the present invention is to provide an improved pressure sensor array wherein the sensitivity of individual pressure sensing regions of the pressure sensor array is adjustable.

A further object of the present invention is to provide improved methods for manufacturing pressure sensor elements or pressure sensor arrays.

A still further object is to provide a pressure sensor array or pressure sensor elements which can be produced with high yields and at a relatively low cost.

These and other objects and advantages are achieved in accordance with the present invention by a pressure sensor element comprising a cathode layer, a cathode operatively connected to a surface of the cathode layer and having a cathode tip at a distal end of the cathode, and an anode diaphragm. The anode diaphragm has a predetermined separation from the cathode tip and receives electrons emitted from the cathode tip.

In one aspect of the present invention, the anode diaphragm is deflectable in response to an applied pressure and electron flow from the cathode tip to the anode varies in accordance with such deflection. An insulating layer insulates and separates the cathode layer from the anode diaphragm and has at least one hole into which the cathode extends. A power supply is operatively connected to the cathode layer and the anode diaphragm for applying a predetermined voltage to produce a predetermined flow of electrons. The magnitude of the flow of electrons depends of the separation between the cathode tip and the anode at the pressure of operation.

In another aspect of the present invention, a plurality of pressure sensor elements are formed on a common cathode layer, thereby forming a pressure sensor array. Addressing means provide means for sensing each of, or selected groups of, the pressure sensor elements within the pressure sensor array. Addressing two or more proximate pressure sensor elements increases the sensitivity of the pressure sensor array in the region where those pressure sensor elements are located.

These and other objects and advantages are achieved in accordance with the present invention by a method for manufacturing pressure sensor elements and arrays comprising the steps of forming a rigid structure by depositing a first insulating layer on a conductive material, depositing a first layer on the first insulating layer, etching a first hole in the first layer and a second hole in the first insulating layer, thereby exposing the conductive material. A cathode is deposited in the second hole on the conductive material, the cathode having a cathode tip at a distal end. A support structure is formed by depositing a conducting layer on a substrate. The rigid structure and support structure are bonded together so that the conducting layer opposes the cathode tip, and the substrate is etched to expose the conducting layer.

BRIEF DESCRIPTION OF THE DRAWINGS

These and other features and advantages of the present invention are disclosed in or apparent from the following detailed description of preferred embodiments. The preferred embodiments are described with reference to the drawings, in which like elements are denoted throughout the figures with like reference numbers, and in which.

DESCRIPTION OF THE PREFERRED EMBODIMENTS

Figure 1A:
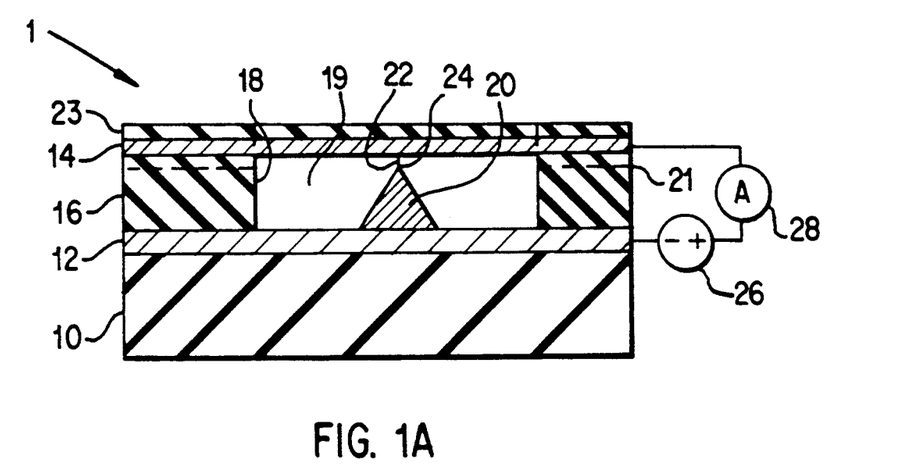
FIG. 1A and 1B are diagrammatic views of a preferred embodiment of a single pressure sensor element according to the present invention.
Figure 1B:
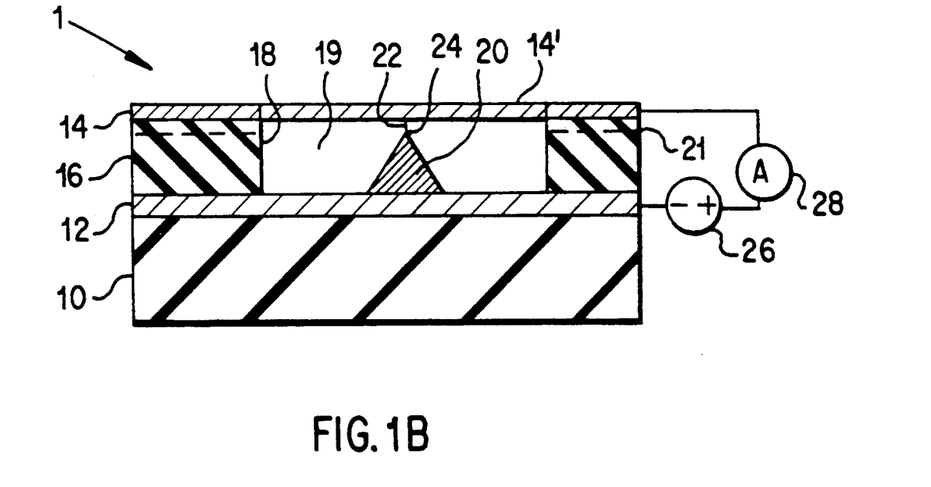

Referring to FIG. 1, a pressure sensor element 1 according to the present invention comprises a substrate 10 formed from a rigid material. The purpose of the substrate 10 is merely to support the operative structure of the pressure sensor element 1 and substrate 10 is omitted if not required for structural reasons. A cathode layer 12 is deposited on the substrate 10 by means described below. In order to form a support structure for an anode layer 14 and to insulate the anode layer 14 from the cathode layer 12, an insulating layer 16 is deposited over the cathode layer 12. Preferably, insulating layer 16 has a uniform thickness and is provided with at least one hole 18, thereby forming a void 19 bounded by the opposing surfaces of the cathode layer 12 and the anode layer 14 and by the circumference of hole 18 in the insulating layer 16. A vent 21 advantageously provides fluid communication from the hole 118 to the exterior of pressure sensor element 1, allowing pressure sensor element 1 to operate at atmospheric pressure. Preferably, a passivating layer 23 is deposited on the surface of the anode layer 14 opposite to void 19.

A single, needle-like cathode 20 is provided in the void 19 with one end of cathode 20 affixed to cathode layer 12. Cathode 20 extends into the void 19 for a predetermined distance which is less than the thickness of the insulating layer 16 and thereby produces a predetermined separation 22 between a cathode tip 24, located on the distal end of the cathode 20, and the side of the anode layer 14 opposing cathode layer 12.

For producing a desired electron emission, a voltage source 26 is operatively connected to both the cathode layer 12 and the anode layer 14. Preferably, the positive and negative terminals of the voltage source 26 are connected to the anode layer 14 and the cathode layer 12, respectively. Voltage source 26 produces a predetermined flow of electrons, i.e., current, whose magnitude is dependant on the separation 22. An ammeter 28 advantageously is connected in series with the voltage source 26 to measure the output of the pressure sensor element 1. Changes in measured current correspond to changes in separation 22.

Figure 2A:
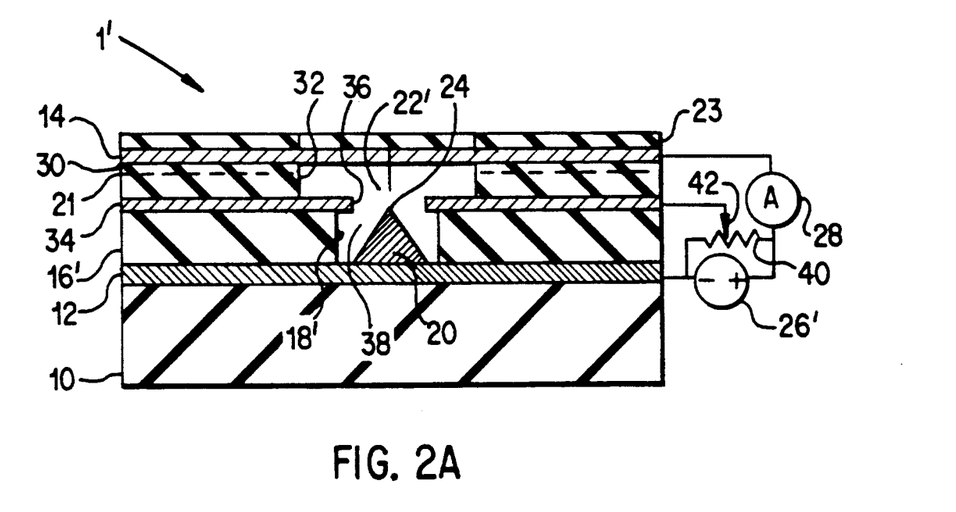
FIG. 2A and 2B are diagrammatic views of another preferred embodiment of a single pressure sensor element according to the present invention.
Figure 2B:
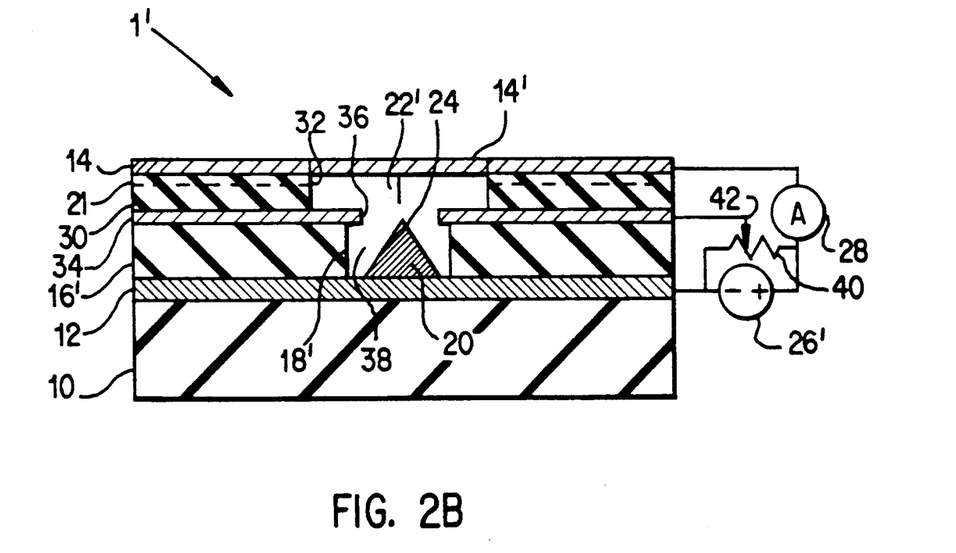

In another preferred embodiment, a pressure sensor element, denoted 1', according to the present invention, comprises substrate 10, cathode layer 12, anode layer 14 and passivating layer 23, as described for the pressure sensor element 1 above. Located between the cathode layer 12 and the anode layer 14 is a support and insulating structure comprised of a first insulating layer 16', deposited over the cathode layer 12, and containing at least one hole (designated 18'). A second insulating layer 30, having at least one hole 32, is formed between the first insulating layer 16' and anode layer 14. Preferably, a gate layer 34 is located between the first and second insulating layers 16' and 30, and contains at least one hole 36. The centerlines of the three holes, 18', 32 and 36, are located approximately on the same axis and, thus, form a void 38 within the pressure sensor element 1'.

A single, needle-like cathode 20 is provided in void 38, having one end of cathode 20 affixed to cathode layer 12. Cathode 20 extends into the void 38 for a predetermined distance which is less than the thickness of the first insulating layer 16', the gate layer 34 and the second insulating layer 30, producing a predetermined separation 22' between cathode tip 24, located on the distal end of the cathode 20, and the side of the anode layer 14 opposing cathode layer 12.

In the preferred embodiment, a voltage source (denoted as 26') is operatively connected to cathode layer 12, gate layer 34 and anode layer 14 to produce a predetermined flow of electrons with a magnitude corresponding to a predetermined separation 22'. Ammeter 28 again measures the output of the pressure sensor element 1'. By way of example, FIG. 2 shows the voltage source 26' connected between the cathode layer 12 and the anode layer 14. A center tap potentiometer 40 is operatively connected in parallel with the output terminals of the voltage source 26' with the center tap 42 connected to the gate layer 34.

The method of operation of the pressure sensor element 1, 1' depends on the predetermined separation 22, 22', respectively. When the separation 22, 22' is less than or equal to about 10 angstroms (Å) electron emission occurs by tunneling. When the separation 22, 22' it greater than about 10 Å, electron emission occurs due to field emission.

Tunneling of electrons from a surface occurs when fields on the order of $10^7$ Volts per centimeter are applied to the surface. For example, a scanning tunneling microscope (STM), such as those described in U.S. Pat. Nos. 4,343,993 and 4,668,865, can be formed when a sharp point is brought close to a surface. The field is accentuated on the sharp point. Tunneling occurs at a potential of a few volts between the point and the surface for a separation of approximately 10 Å. In STM technology, a voltage is applied to produce tunneling of electrons, and the tip is scanned across the surface while maintaining a constant tunneling current. Because the surface being examined has topography, the sharp point must be moved towards or away from the surface to maintain a constant spacing and, therefore, a constant tunnel current. A map of the surface is then obtained by plotting the separation. Since the current produced by the tunneling of electrons is exponentially dependant on the separation between the tip and the surface, surface definition is measured with a high degree of accuracy. With STM techniques, it is possible to resolve surface features of about 0.02 Å.

If the cathode-to-anode separation is greater than about 10 Å, the mechanism of electron emission is called field emission. The current density, J, is described by the Fowler-Nordheim equation:

$$J = A \frac{(\beta V)^2}{\phi} \exp - \frac{B\phi^{3/2}}{\beta V}$$

where $\phi$ is the work function, V is voltage, $\beta$ is a geometric factor and A and B are constants. In field emission, the electrons leave the metal cathode and travel the air or vacuum gap before penetrating the anode.

For the pressure sensor element 1, 1', described above, the electron emission mechanism, tunneling or field emission, is determined by the predetermined separation 22, 22', which is controlled by the fabrication techniques selected in building the pressure sensor element 1,1'. In either case, the method for pressure detection depends on the field strength between the cathode tip 24 and the anode layer 14. The anode layer 14 for the pressure sensor element 1, 1' is fabricated as a flexible diaphragm (denoted as anode diaphragm 14' and shown in FIGS. 1B and 2B) which deflects in response to the pressure applied to the anode layer 14. The deflection of anode diaphragm 14' changes the actual separation between anode layer 14 and cathode tip 24, which changes the field strength and, thus, causes a corresponding change in the quantity of electron current produced by the predetermined applied voltage. In actual operation, the substrate 10, the cathode layer 12 and the support structure, insulating layer 16 or first and second insulating layers 16', 30 and gate layer 34, form a rigid structure. Pressure applied to the pressure sensor element 1, 1' at the anode layer 14 causes the anode diaphragm 14' to deflect into the void 19 (void 38), changing the magnitude of separation 22, 22', and, thus, changing the field strength between the cathode tip 24 and the anode layer 14. (Hereinafter, the anode layer 14 having anode diaphragms 14' will be referred to using the terminology anode (diaphragm) layer 14 unless more specific terms are needed to distinguish the anode diaphragm 14' region from the anode layer 14). This in turn produces a measurable change in electron current which is detected by the ammeter 28.

The deflection of the anode (diaphragm) layer 14 is a stress reaction, and, thus, the sensitivity of the pressure sensor element 1, 1' is determined by the physical properties of the material used in fabricating anode (diaphragm) layer 14, and the surface area of the void 19 is separation 22, 22', and since the emitted current is exponentially dependant of field strength, a high degree of sensitivity is achieved by pressure sensor element 1, 1'.

While the preferred embodiments of the pressure sensor element 1, 1' are described in terms of measuring an applied pressure by measuring the change in electron current using ammeter 28, other mechanisms are not precluded by this description. For example, in another preferred embodiment, the voltage source 26 advantageously is a voltage device where the output voltage is servoed such that the electron current is maintained at a predetermined constant value. Deflection of the anode (diaphragm) layer 14 causes a resultant change in the voltage applied by voltage source 26, 26' and the pressure change is determined by measuring the change in supply voltage.

It should be further understood that the teachings of the present application are not limited to sensing pressure. The present invention is equally applicable for use in detecting any external stimulus capable of directly or indirectly causing a change in the actual separation between the cathode tip 24 and the anode (diaphragm) layer 14. For example, in yet another preferred embodiment, the anode (diaphragm) layer 14 comprises first and second materials having thermal expansion coefficients different from each other, forming a bimetallic sandwich material. The anode (diaphragm) layer 14 advantageously is rendered temperature sensitive, since changes in temperature cause the materials to expand differing amounts and, thus, cause the anode (diaphragm) layer 14 to bend, changing the actual separation between the cathode tip 24 and the anode (diaphragm) layer 14. In still other preferred embodiments, secondary structures such as beams and weights are fabricated on anode (diaphragm) layer 14 so that vibrations or velocity changes cause resultant changes in the anode (diaphragm) layer 14 position relative to the cathode tip 24. Thus, microphones and accelerometers advantageously are produced from the basic structure of the present invention. In still further preferred embodiments, secondary structures are fabricated to place hygroscopic elements, which expand or contract according to changes in moisture, in contact with the anode (diaphragm) layer 14 to thereby render the present invention responsive to changes in humidity.

In another preferred embodiment of the present invention, a plurality of pressure sensor elements 1, 1', described above, advantageously form two dimensional pressure sensor arrays, which measure pressure distributions.

Figure 3:
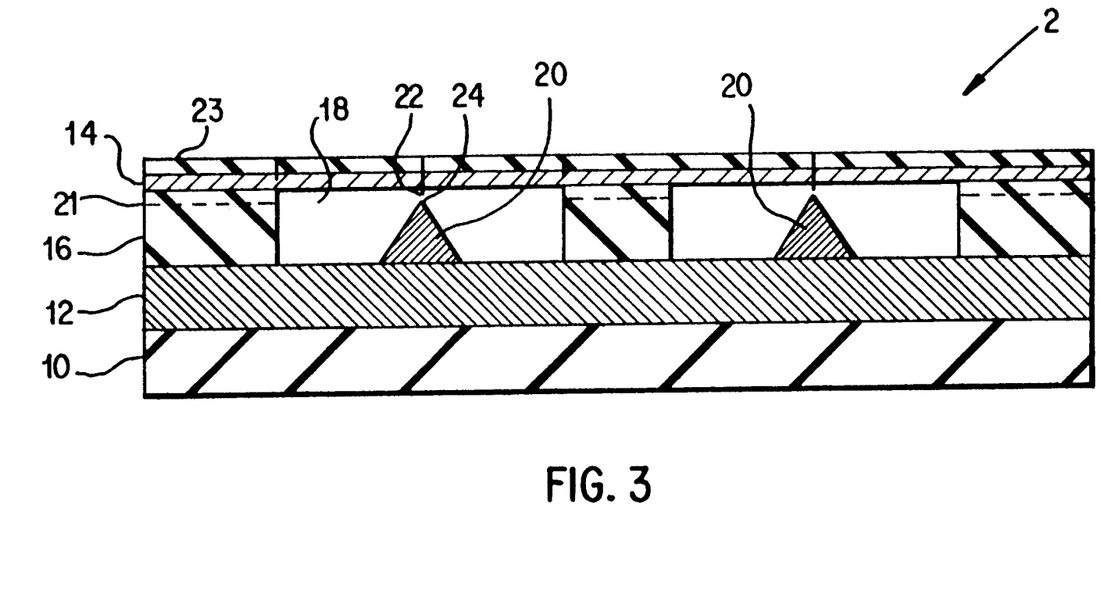
FIG. 3 is a diagrammatic view of a preferred embodiment of a pressure sensor array using a plurality of pressure sensor elements as shown in FIG. 1A.

Referring to FIG. 3, a pressure sensor array 2 according to the present invention comprises a plurality of the pressure sensor elements 1 located in an array. Since only the actual number of pressure sensor elements 1 changes between FIGS. 1 and 3, additional discussion of the details and arrangement of the various layers and elements will be omitted. It should be noted, however, that insulating layer 16 is provided with a plurality of holes 18, forming a cellular grid or mesh pattern. While not limited to any particular pattern, the structure will be further described in terms of parallel rows and columns perpendicular to each other, for ease of visualization. Preferably, the holes 18 in the cellular grid are arranged in a hexagonal close-pack arrangement, which provides a maximum density of pressure sensor elements 1 in pressure sensor array 2.

Figure 4:
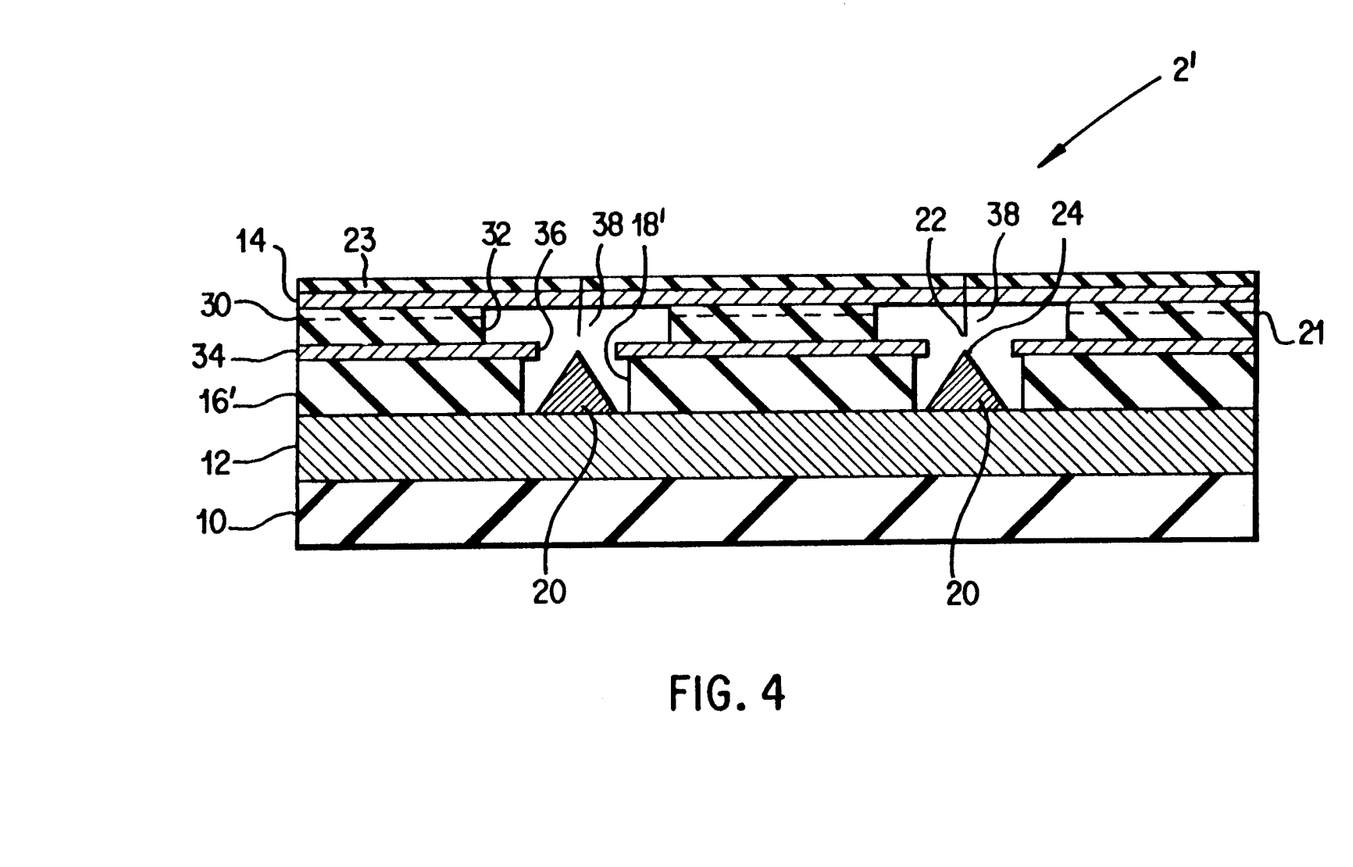
FIG. 4 is a diagrammatic view of another preferred embodiment of a pressure sensor array using a plurality of pressure sensor elements as shown in FIG. 2A.

Referring to FIG. 4, another preferred embodiment of the present invention is shown in FIG. 4, wherein a pressure sensor array, denoted 2', comprises a plurality of the triode pressure sensor elements 1'. The centerlines of the three holes, 18', 32 and 36, are located approximately on the same axis and, thus, form a cellular array of voids 38 within the pressure sensor array 2'.

Preferably, pressure sensor array 2, 2', described above, contains a plurality of pressure sensor elements 1, 1', respectively, connected in parallel. Pressure sensor array 2, 2' advantageously is configurable for mapping pressure after certain modifications are made to the structures described above to address the individual pressure sensor elements 1, 1', or predetermined groups of the pressure sensor elements 1, 1'. While each individual pressure sensor element 1, 1' can be fabricated such that individually wired to the voltage source 26, 26' and an ammeter 28, more efficient methods of addressing are available. For example, array addressing and charged coupled device addressing advantageously are used to discriminate between the individual pressure sensor elements 1, 1' of the pressure sensor array 2, 2'.

Figure 5A:
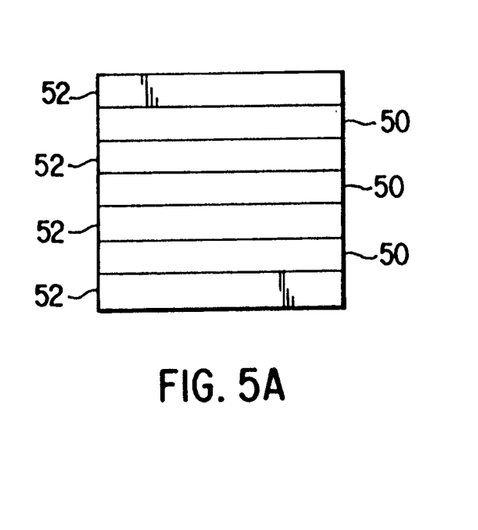
FIGS. 5A, 5B, and 5C are schematic views of patterns formed on the cathode and anode layers for accomplishing addressing of the pressure sensor elements shown in FIGS. 1A, 2A, 3 and 4.
Figure 5B:
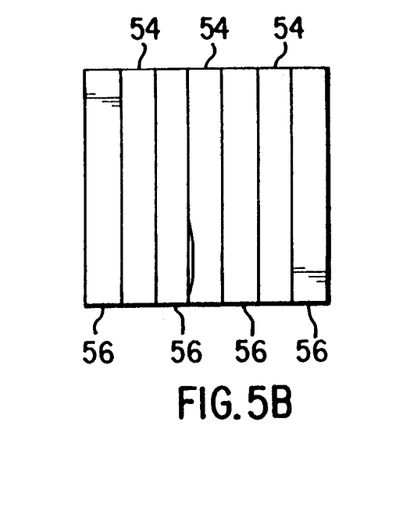
Figure 6A:
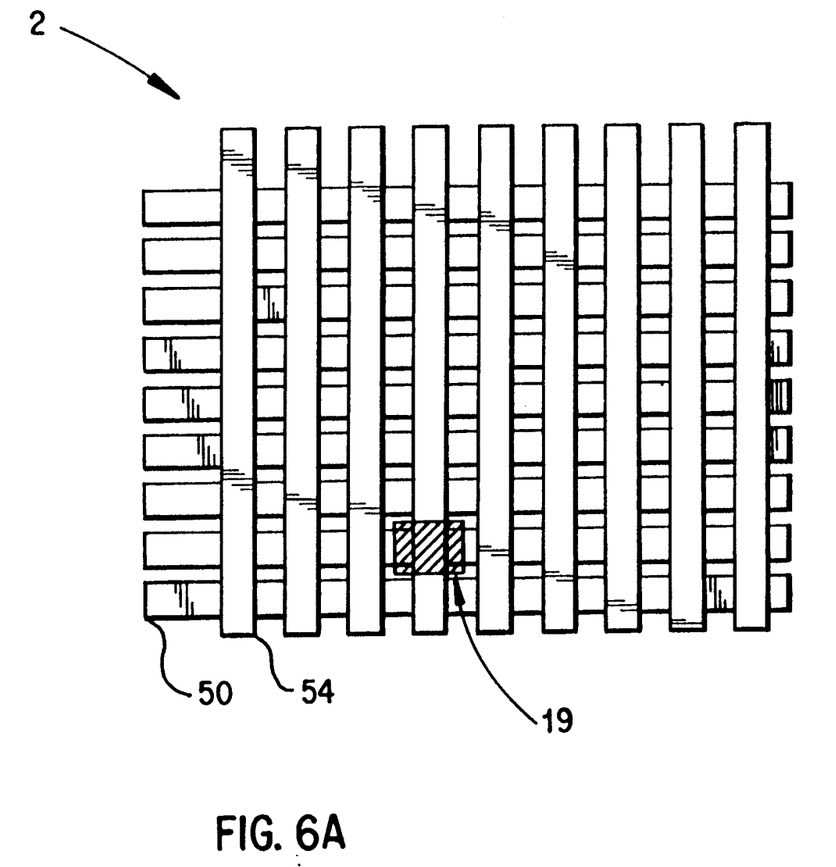
FIGS. 6A and 6B are schematic views of structures for accomplishing pressure sensor array addressing in accordance with FIGS. 5A and 5B and FIGS. 5A and 5C, respectively.

For array addressing, both the cathode layer 12 and the anode (diaphragm) layer 14 are formed having predetermined patterns of conducting and insulating materials. FIG. 5A shows cathode layer 12 comprising parallel strips of conducting material 50 and insulating material 52. FIG. 5B shows anode (diaphragm) layer 14 comprising parallel strips of conducting material 54 and insulating material 56. A pressure sensor array 2, 2' thus formed produces the structure shown in FIG. 6A. Each pressure sensor element 1, 1' of the pressure sensor array 2, 2' advantageously is addressed by merely specifying the row and column to be read.

The actual number of pressure sensor elements 1, 1' addressed in this manner is controlled by varying the width of the conducting strips comprising cathode layer 12 and anode (diaphragm) layer 14. For example, if each line separation between two adjacent pressure sensor elements 1, 1', the intersection of the rows and columns encompasses four individual pressure sensor elements 1, 1' and the value read by array addressing is the output of the four devices in parallel. Operating a plurality of pressure sensor elements 1, 1' in parallel advantageously increases the sensitivity of pressure sensor array 2, 2' by increasing the measurable current produced by the flow of electrons. According to another aspect of the present invention, sensitivity is increased by forming a plurality of cathodes in each of the voids 19, 38 thereby increasing the measurable current.

Figure 5C:
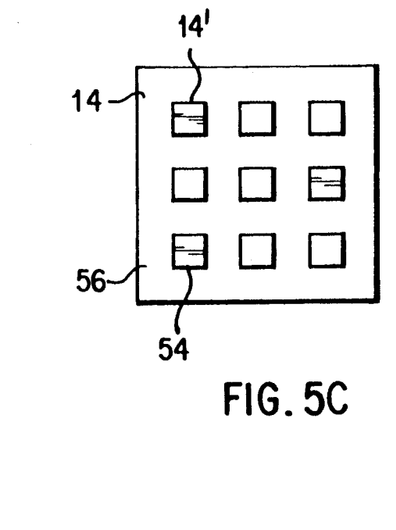
Figure 6B:
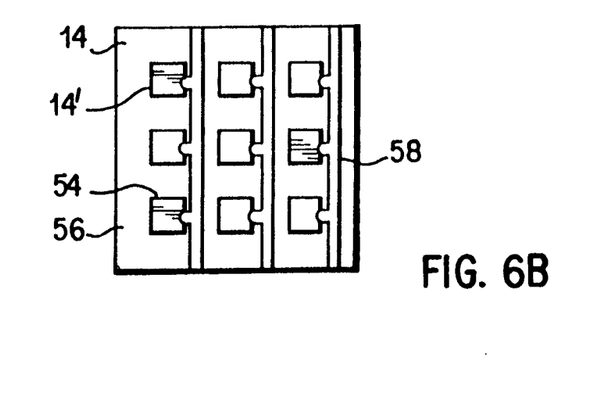

In another preferred embodiment of the present invention, conducting strips having different geometries produce different physical structures to accomplish array addressing. Referring to FIG. 5C, an exemplary anode (diaphragm) layer 14 is shown formed from a plurality of anode diaphragms 14' located in anode layer 14. Anode layer 14 is formed as a mesh or grid pattern of insulating material 56 and individual anode diaphragms 14' are formed in the apertures of the pattern from conducting material 54. A connector strip 58, shown in FIG. 6B, is formed on the surface of anode layer 14 substantially over the insulating material 56. A portion of the connecting strip 58 is connected to at least one of the anode diaphragms 14'. Preferably, array addressing is accomplished using the conducting strips 50, shown in FIG. 5A, of the cathode layer 12 and the connecting strips 58.

Figure 7:
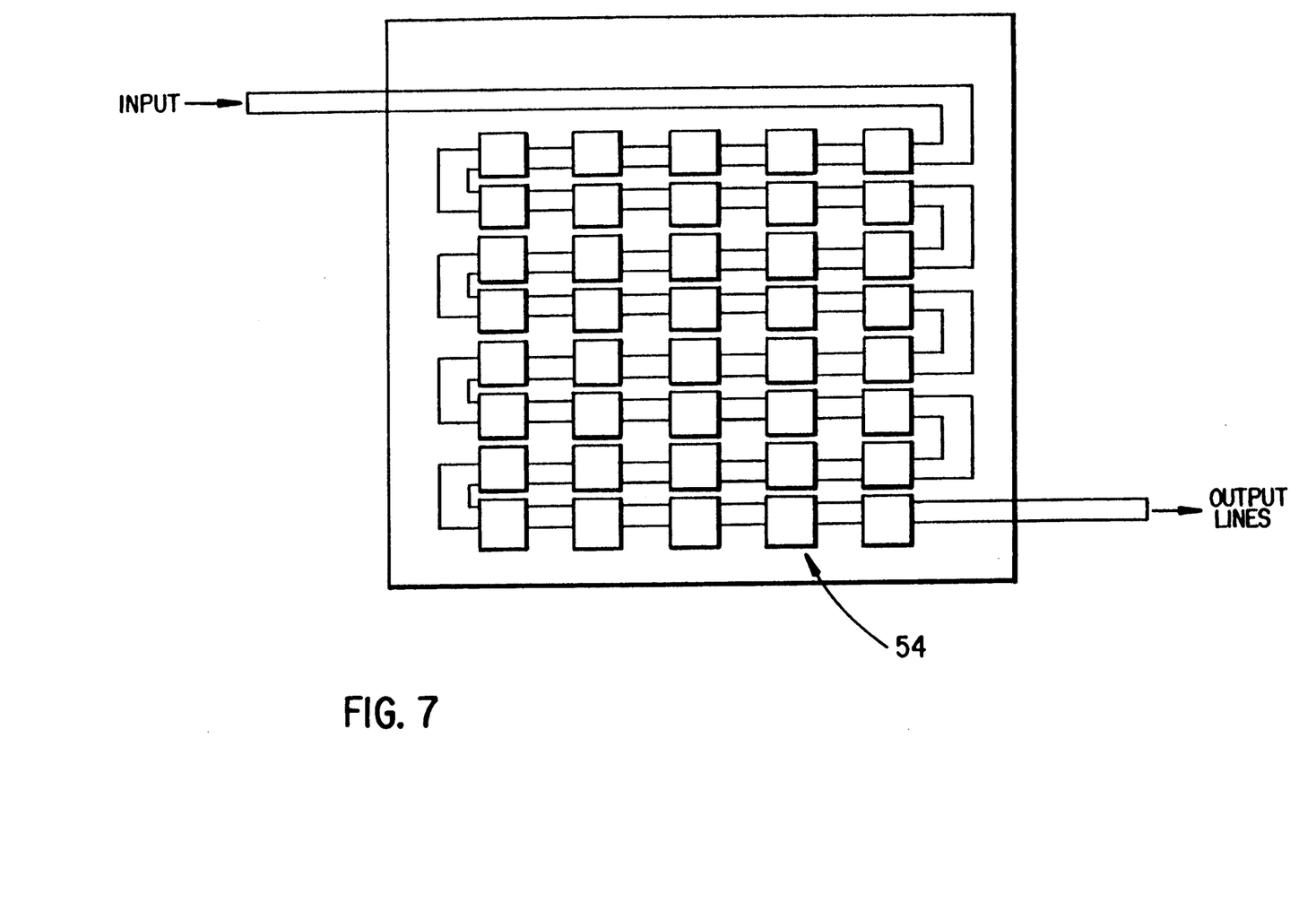
FIG. 7 is a schematic view showing charge-coupled device addressing of a preferred embodiment of the pressure sensor array.

In another preferred embodiment of the present invention, conventional charge-coupled device (CCD) addressing advantageously is used to sample the pressure sensed at each pressure sensor element 1, 1' of the pressure sensor array 2, 2'. Preferably, addressing each pressure sensor element 1, 1' is performed using, for example, buried-channel CCD addressing in a pattern such as that shown in FIG. 7. Since CCD addressing is a conventional technique used for such devices as video cameras and facsimile machines, and since the fabrication of buried-channel CCDs does not constitute a part of the present invention, further details on CCDs are not given here.

The methods of fabricating pressure sensor elements and sensor element arrays will now be discussed while referring to FIGS. 8 and 9, which show the resulting structures of the pressure sensor arrays 2,2' after various fabrication steps.

Figure 8A:
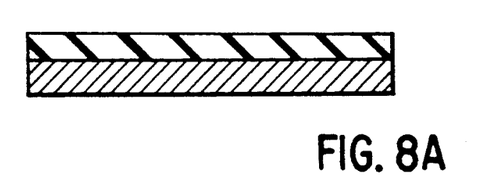
FIGS. 8A–8C schematically illustrate the steps of forming a pressure sensor array in accordance with a preferred embodiment of the present invention.

The method for fabricating a two active layer device, previously described as the pressure sensor element and the pressure sensor array 2 will now be described. A rigid structure is formed by depositing a first insulating material 16 onto a conductive material 12 to a thickness of about 1 micrometer ($\mu$m) by conventional techniques including thermal oxidation, chemical vapor deposition (CVD) or other deposition technique. The resulting structure is illustrated in FIG. 8A.

Figure 8B:
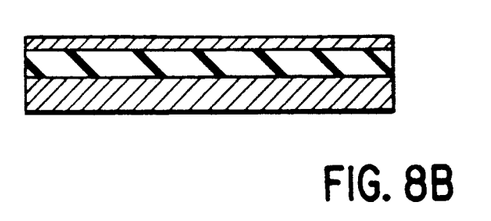

A layer 34 is then deposited to a thickness of about 3000 Å on the first insulating layer 16 as shown in FIG. 8B. Preferably, layer 34 is conductive. A layer of resist material is then applied to a uniform thickness over layer 34 using any conventional technique. A pattern of apertures having diameters approximately equal to the thickness of the first insulating layer 16 and centerlines corresponding to the centerlines of the desired cathode locations are then developed in the resist layer. The resist material corresponding to the intended holes 18 is then removed by conventional techniques.

First holes are produced by etching layer 34 through the apertures in the resist layer using conventional etching techniques and then second holes are formed in the insulating layer 16, exposing the conductive material 12, by directional plasma etching. The remaining resist layer is then removed and layer 34 is undercut using a conventional process, e.g., isotropic wet etching. The resulting structure is shown by FIG. 8C.

Figure 8C:
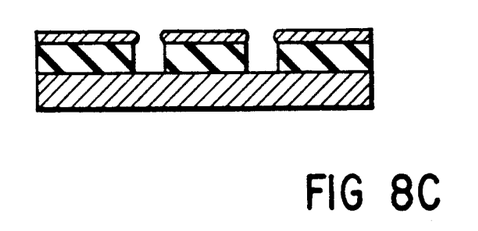
Figure 8D:
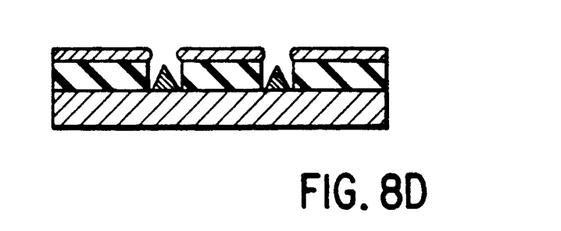

Cathodes 20 are deposited in the second holes shown in FIG. 8C using methods disclosed by Spindt et al., U.S. Pat. Nos. 3,789,471 and 3,812,5591, incorporated herein for all purposes by reference. The height of the cathodes 20 thus formed are controlled so that cathode tips 24 at the distal end of the cathodes 20 are within a plane parallel to conducting material 12. Preferably, this plane is offset from the insulating layer 16, conducting layer 34 boundary by separation 22. The resulting structure is shown by FIG. 8D.

Figure 8E:
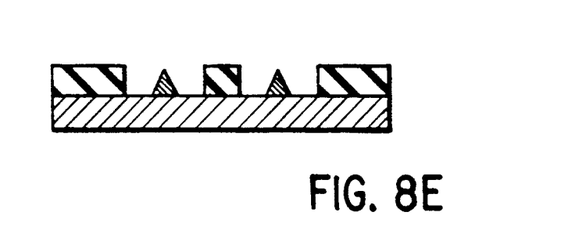

The second holes in the insulating layer 16 are further undercut to the desired diameter of the anode diaphragm 14' by a second conventional isotropic wet etch step. The remainder of layer 34 is then removed by selectively etching layer 34, leaving insulating layer 16 and cathodes 20 exposed. The resulting structure is shown by FIG. 8E. A vent hole is then formed by conventional techniques including: applying a resist layer to insulating layer 16; developing a line in the resist layer; washing; etching a line in insulating layer 16; and then selectively etching the remaining resist layer.

A support structure containing the anode (diaphragm) layer 14 is formed by depositing a conducting layer on an independent flat substrate. The resulting structure is shown in FIG. 8F.

Figure 8F:
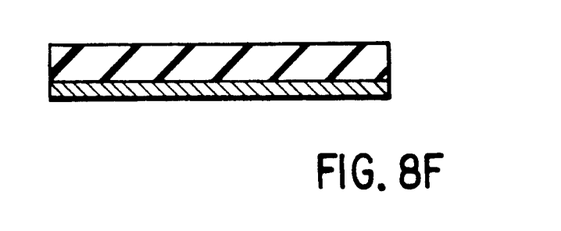
Figure 8G:
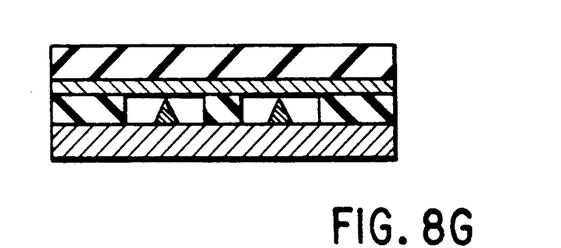

The individual pieces, the rigid structure and the support structure shown in FIGS. 8E and 8F, are then assembled by bonding the anode (diaphragm) layer 14 to the insulating layer 16 using conventional techniques, i.e., anodic or fusion bonding techniques. The resulting structure is shown in FIG. 8G. The substrate material adjacent to anode (diaphragm) layer 14 is then selectively etched to leave the rigid structure bonded to the anode (diaphragm) layer 14, producing the structure shown in FIG. 3. Preferably, a passivating layer 23 is deposited on the anode (diaphragm) layer 14 to protect the anode (diaphragm) layer 14 from physical damage, as passivating layer 23 is the actual layer subjected to the external stimulus.

Figure 9A:
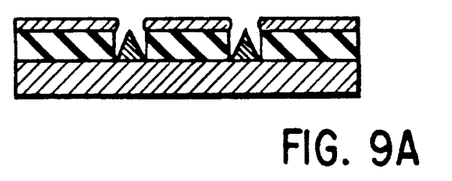
FIGS. 9A–9B schematically illustrate the steps of forming a pressure sensor array in accordance with another preferred embodiment of the present invention.

In another preferred embodiment of the method of the present invention, pressure sensor elements 1' and pressure sensor array 2' are formed by a method similar to that described immediately above. Preferably, fabrication is the same up to the point where cathodes 20 are deposited in the second holes. The height of the cathodes formed is controlled so that the cathode tips 24 are again located in a plane parallel to the conducting material 12. Preferably, the plane of the cathode tips 24 is proximate to the plane of layer 34. An exemplary structure is shown by FIG. 9A.

Figure 9B:
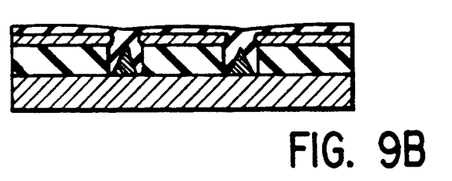

An insulating layer 30 is then deposited on layer 34 to a predetermined thickness so that the distance from the cathode tips 24 to the surface of the anode (diaphragm) layer 14, located opposite layer 34 after fabrication is complete, will be the predetermined separation 22'. An exemplary structure is shown in FIG. 9B. The second insulating layer 30 is then patterned using conventional techniques to produce third holes whose centerlines correspond to the centerlines of the first and second holes. Preferably, the diameter of the third holes formed in the second insulating layer 30 is the width of the anode diaphragms 14'. The resulting structure is shown by FIG. 9C.

A vent is then formed by the steps of: applying a resist layer to the second insulating layer 30; developing a line in the resist layer; washing; etching a line in the second insulating layer 30; and then selectively etching the remaining resist layer, thereby exposing the second insulating layer 30.

In one aspect of the present invention, a support structure containing the anode (diaphragm) layer 14 is formed by depositing conducting layer on an independent flat substrate. The resulting structure is shown in FIG. 9D.

Figure 9C:
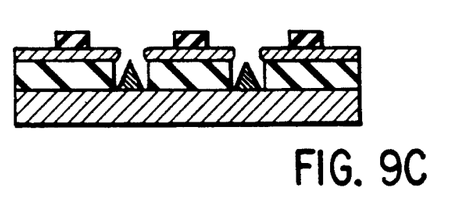
Figure 9D:
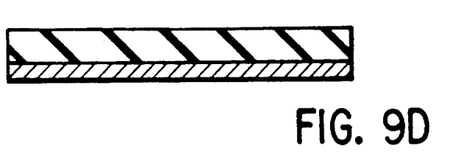
Figure 9E:
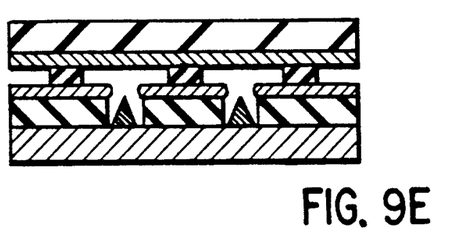

The individual pieces, the rigid structure and the support structure, shown in FIGS. 9C and 9D, respectively, are then assembled by bonding the anode (diaphragm) layer 14 to the second insulating layer 30 using conventional techniques, i.e., anodic or fusion bonding techniques. The resulting structure is shown in FIG. 9E. Preferably, the substrate material adjacent to anode (diaphragm) layer 14 is then selectively etched to leave the rigid structure bonded to the anode (diaphragm) layer 14, producing the structure shown in FIG. 4. A passivating layer 23 advantageously is deposited by conventional techniques. The passivating layer 23 is the surface which is actually in contact with the surface to be sensed.

In yet another preferred embodiment of pressure sensor element 1', which advantageously is used to form sensor array 2', a power source 26' is operatively connected to cathode layer 14, anode layer 14 and gate layer 34. A first predetermined voltage is applied between cathode layer 12 and gate layer 34, producing a predetermined flow of electrons between cathode tip 24 and gate layer 34 and a predetermined first potential at cathode tip 24. Preferably, a second predetermined voltage is applied so as to produce a second potential at anode layer 14 which is less than or equal to the cathode tip 24 potential. The field at cathode tip 24 advantageously is a superposition of both the first and second potentials. Deflection of anode layer 14, which produces a corresponding decrease in separation 22', produces a corresponding decrease in the flow of electrons from cathode tip 24. Preferably, ammeter 28 measures the current resulting from the flow of electrons. Thus, current from cathode tip 24 initially is a maximum value and decreases with increasing deflection of anode layer 14.

Those skilled in the art will recognize that various fabrication alternatives may be used without departing from the disclosure of the invention. In another preferred embodiment, for example, the substrate material on which the anode (diaphragm) layer 14 is deposited is first patterned and etched by conventional techniques to form linear strips or channels, described above. Conventional deposition techniques are then used to deposit the selected anode diaphragm 14 material into the strips thus formed. Bonding of the substrate/anode layer is then performed as described above.

Those skilled in the art will also recognize that, although the discussion above was made in terms of fabricating either a pressure sensor element or a pressure sensor array, in actuality, individual pressure sensor elements 1, 1' advantageously are obtained from pressure sensor arrays 2,2'. By controlling the geometry of the pressure sensor array 2, 2', individual pressure sensor elements 1, 1' can be fabricated at substantial cost savings and in production quantities.

In addition, those skilled in the art will recognize the flexibility of the above described sensors for performing applications not specifically addressed. For example, the pressure sensor array 2, 2' is easily adapted to other applications such as artificial skin for robotic assemblies, and scanners for reading surface contours of small parts, finger prints and the like. In other preferred embodiments, the sensor array is made to sense a variety of external stimuli simultaneously by fabricating various functions into different regions of anode (diaphragm) layer 14. Thus, an exemplary combined sensor advantageously is produced for sensing two or more stimuli, i.e., pressure and temperature, at different, but closely spaced, regions on the array.

Other modifications and variations to the invention will be apparent to those skilled in the art from the foregoing disclosure and teachings. Thus, while only certain embodiments of the invention have been specifically described herein, is will be apparent that numerous modifications may be made thereto without departing from the spirit and scope of the invention.

What is claimed is:

1. A sensor apparatus comprising:
   cathode means for emitting electrons responsive to a predetermined first voltage;
   support means for supporting said cathode means;
   anode means for collecting said electrons;
   insulating means located between said cathode means and said anode means, for insulating and separating said anode means from said cathode means such that said anode means has a predetermined separation from said cathode means and such that said anode means is deflectable with respect to said cathode means responsive to an external stimulus, wherein the number of said electrons increases as said separation between said anode means and said cathode means decreases and the number of said electrons decreases as said separation increases; and
   gate means disposed between said cathode means and said anode means for receiving a predetermined second voltage for use in controlling field strength proximate to said cathode means.

2. The apparatus of claim 1, wherein said external stimulus is indicative of at least one of pressure, temperature, humidity and acceleration.

3. The apparatus of claim 1, wherein said anode means is produced from one of a conducting material, a metal and a bimetallic sandwich material.

4. The apparatus of claim 1, wherein said separation is greater than about 10 angstroms.

5. The apparatus of claim 1, wherein said insulating means comprises first and second means for insulating and separating said cathode means from said gate means and said gate means from said anode means, respectively.

6. The apparatus of claim 1, wherein said cathode means comprises a cathode tip opposed to said anode means.

7. A sensor apparatus, comprising:
a cathode layer;
an anode layer located substantially parallel to said cathode layer;
at least one cathode operatively attached to said cathode layer, said at least one cathode having a cathode tip at a distal end;
insulating means located between said cathode layer and said anode layer, for insulating and separating said anode layer from said cathode layer such that said anode layer has a predetermined separation from said cathode tip for receiving electrons emitted from said cathode tip and such that said anode layer is deflectable in response to an external stimulus; and
means for receiving a predetermined first voltage producing a flow of electrons having a magnitude dependent on said separation.

8. The apparatus of claim 7, wherein said insulating means comprises an insulating layer located between said anode layer and said cathode layer for insulating and separating said anode layer from said cathode layer, said insulating layer having at least one hole located substantially coaxial with the axis of said at least one cathode tip.

9. The apparatus of claim 7, wherein said insulating means comprises first and second insulating layers located between said anode layer and said cathode layer for insulating and separating said anode layer from said cathode layer, said first and second insulating layers having at least one first and second hole, respectively, located substantially coaxial with the axis of said at least one cathode tip, and wherein the apparatus further comprises a gate layer located between said first and second insulating layers and having at least one third hole substantially coaxial with the axis of said at least one cathode tip, said gate layer receiving a predetermined second voltage for use in controlling field strength at said cathode tip.

10. The apparatus of claim 7, wherein said anode layer deflects towards said at least one cathode tip responsive to said external stimulus.

11. The apparatus of claim 7, wherein said separation is greater than about 10 Å.

12. The apparatus of claim 7, wherein said external stimulus is selected from the group consisting of temperature, humidity, pressure and acceleration.

13. A pressure sensor apparatus, comprising:
a cathode layer;
an cathode operative connected to a surface of said cathode layer and having a cathode tip at a distal end of said cathode;
an anode diaphragm located substantially parallel to said cathode layer;
an insulating layer located between said cathode layer and said anode diaphragm and separating said cathode layer from said anode diaphragm such that said anode diaphragm has a predetermined separation from said cathode tip for receiving electrons emitted from said cathode tip, said insulating layer having at least one hole into which said cathode extends, said anode diaphragm being deflectable in response to a pressure applied to said anode diaphragm; and
means for applying a predetermined voltage producing a flow of electrons having a magnitude dependent on said separation.

14. The apparatus of claim 13, further comprising a vent means for producing fluid communication between said at least one hole and the atmosphere.

15. The apparatus of claim 13, wherein said anode diaphragm is a metal.

16. The apparatus of claim 13, wherein said predetermined separation is greater than about 10 Å.

17. The apparatus of claim 13, wherein said electrons are emitted by tunneling.

18. A pressure sensor apparatus, comprising:
a cathode layer;
an cathode operatively connected to a surface of said cathode layer and having a cathode tip at a distal end of said cathode;
an anode diaphragm located substantially parallel to said cathode layer;
a gate layer located between said cathode layer and said anode diaphragm and substantially parallel to said cathode layer and having at least one first hole substantially coaxial with the axis of said cathode tip;
a first insulating layer separating said cathode layer from said gate layer, said first insulating layer having at least one second hole into which said cathode extends;
a second insulating layer separating said gate layer from said anode diaphragm such that said anode diaphragm has a predetermined separation from said cathode tip for receiving electrons emitted from said cathode tip, said second insulating layer having at least one third hole substantially coaxial with the axis of said cathode, said anode diaphragm being deflectable in response to a pressure applied to said anode diaphragm; and
means for applying a plurality of predetermined voltages to said cathode layer, said gate layer and said anode diaphragm to produce a flow of electrons having a magnitude which varies according to the separation between said cathode tip and said anode diaphragm.

19. The apparatus of claim 18, further comprising a vent means for producing fluid communication between said third hole and atmosphere.

20. The apparatus of claim 18, wherein said anode diaphragm is a metal.

21. The apparatus of claim 18, wherein said predetermined separation is greater than about 10 Å.

22. The apparatus of claim 18, wherein said electrons are emitted by tunneling.

* * * * *